(12) United States Patent
Goetz et al.

(10) Patent No.: US 11,000,371 B2
(45) Date of Patent: May 11, 2021

(54) APPARATUS COMPRISING AN ALIGNING DEVICE, SET AND METHOD

(71) Applicant: Venus Medtech (Hangzhou) Inc., Hangzhou (CN)

(72) Inventors: Wolfgang Goetz, Regensberg (DE); Hou-Sen Lim, Singapore (SG)

(73) Assignee: Venus Medtech Hangzhou Inc, Hangzhou (CN)

(*) Notice: Subject to any disclaimer, the term of this patent is extended or adjusted under 35 U.S.C. 154(b) by 262 days.

(21) Appl. No.: 16/174,716

(22) Filed: Oct. 30, 2018

(65) Prior Publication Data

US 2019/0060066 A1 Feb. 28, 2019

Related U.S. Application Data

(63) Continuation of application No. 13/994,705, filed as application No. PCT/EP2011/006253 on Dec. 12, 2011, now abandoned.

(51) Int. Cl.
*A61F 2/24* (2006.01)
*A61F 2/95* (2013.01)

(52) U.S. Cl.
CPC .......... *A61F 2/2427* (2013.01); *A61F 2/2439* (2013.01); *A61F 2/95* (2013.01); *A61F 2/2418* (2013.01); *A61F 2250/0096* (2013.01)

(58) Field of Classification Search
CPC ...... A61F 2/243; A61F 2/2433; A61F 2/2436; A61F 2/2439; A61F 2/246; A61F 2/2466; A61F 2/962; A61F 2/966; A61F 2002/821; A61B 2017/00575; A61B 2017/00783; A61B 2017/00986
See application file for complete search history.

(56) References Cited

U.S. PATENT DOCUMENTS

| | | | | |
|---|---|---|---|---|
| 2004/0059351 A1* | 3/2004 | Eigler | ............... | A61B 17/0469 606/148 |
| 2006/0030867 A1* | 2/2006 | Zadno | ............... | A61B 17/0644 606/142 |

* cited by examiner

*Primary Examiner* — Katherine M Shi
*Assistant Examiner* — Lindsey Bachman
(74) *Attorney, Agent, or Firm* — Raymond Sun

(57) ABSTRACT

The present invention relates to an apparatus (3) for use during implanting at least one medical implant (6) at an implantation site within a patient's body, wherein the apparatus (3) comprises an aligning device (9) for aligning the apparatus (3) at the implantation site, wherein the aligning device (9) is capable of being transferred from a non-aligning position into an aligning position. It further relates to a set and a method.

20 Claims, 3 Drawing Sheets

APPARATUS COMPRISING AN ALIGNING DEVICE, SET AND METHOD

The present invention relates to an apparatus according to claim 1 for inserting an implant and a set according to claim 11. It further relates to a method according to claim 12.

From practice, implants for replacing or supporting body functions (such as, e.g., stents) are known that are inserted into the patient's body by means of an apparatus in case of complex or difficult, respectively, conditions of orientation such as an insufficient direct sight onto the implantation site.

One object of the present invention is to suggest an apparatus for orienting during implanting or for aligning an implant or an apparatus for implanting the implant. Furthermore, an appropriate set comprising such an apparatus and a method are proposed.

This object is solved by an apparatus having the features of claim 1.

Thus, according to the invention, an apparatus for use during implanting at least one medical implant at an implantation site in a patient's body is proposed, wherein the apparatus comprises an aligning device for aligning the apparatus at the implantation site, wherein the aligning device is capable of being transferred from a non-aligning position into an aligning position.

The object according to the invention is further solved by a set comprising at least one apparatus according to the invention and at least one implant.

The object according to the invention is further solved by a method comprising using an apparatus according to the invention and/or a set according to the invention.

Advantageous embodiments of the apparatus according to the invention are each subject-matter of the dependent claims.

In certain embodiments, aligning the apparatus according to the invention is alternatively or additionally understood as aligning the medical implant.

In some embodiments according to the invention, aligning is alternatively or additionally understood as orienting the apparatus or the medical implant such that a user of the apparatus according to the invention is aware of the position of the apparatus and/or the implant relative to a body tissue or a body structure or an anatomic condition of the implantation site, respectively, after aligning or that the user is given a corresponding hint by means of the alignment.

In certain embodiments according to the invention, aligning is understood as aligning the apparatus and/or the medical implant.

In certain embodiments according to the invention, the aligning device is capable of being transferred from the aligning position into the non-aligning position as well.

In one embodiment of the apparatus according to the invention, the aligning device is or comprises a wire or a filament, respectively.

In the following, the term "wire" or "filament", respectively, may also define a plurality of wires or filaments, respectively, whenever a person skilled in the art recognizes the exchangeability of the terms.

In some embodiments according to the invention, the aligning device comprises a through opening or passage opening, respectively, in at least one section thereof.

In certain embodiments according to the invention, the through opening extends along the aligning device or a section thereof. The through opening may be present in an interior of the aligning device. It can be intended or provided and/or serve for transporting or guiding or directing a fluid from one end of the aligning device or of the section thereof to another end portion of the aligning device or of the section.

In one embodiment of the apparatus according to the invention, the through opening is penetrable or permeable, respectively, for fluids in its longitudinal direction. The term "penetrable" or "permeable", respectively, hereby refers to the ability of the aligning device to be flown through by fluids and/or to guide the said.

In certain embodiments according to the invention, the aligning device is movable—namely either as a whole or in sections thereof—relative to the apparatus according to the invention.

According to the invention, "movable" may also be understood as "slidable". A corresponding support may be provided, but does not have to be provided. A corresponding material combination may be provided, but does not have to be provided.

In one embodiment according to the invention, the apparatus is tubular (i.e., having a hollow interior), such as, e.g., a hollow cylinder having a through opening in or along its interior. The apparatus may be designed symmetrically or asymmetrically, both relative to its through direction and also in another direction, in particular in a direction or plane perpendicular to the through direction.

In one embodiment according to the invention, a shaft of the apparatus is penetrable or permeable, respectively, in its interior in at least sections of its longitudinal direction. The shaft comprises a wall. The shaft comprises at least one shaft opening or shaft aperture, respectively. The at least one shaft aperture is preferably not arranged at the front side but at or on a lateral or envelop surface of the shaft. The shaft aperture is preferably a through opening establishing a connection between the interior and an exterior of the shaft of the apparatus. In certain embodiments according to the invention, the aligning device can be delivered or passed or transferred from the non-aligning position into the aligning position through the shaft aperture.

In one embodiment according to the invention, the shaft of the apparatus comprises a plurality of shaft apertures that are evenly or unevenly spaced around or across a periphery or a lateral surface of the shaft. Additionally or alternatively, the shaft apertures may be dispersed along a longitudinal direction of the shaft.

Sections of the aligning device may enter and/or exit through the shaft apertures.

In some embodiments according to the invention, the aligning device comprises two or more aligning sections that may be actuated independently from each other such that they can contact the tissue of the implantation site or of the implantation organ or of the organ independently from each other, respectively.

For this purpose, the aligning sections are in some embodiments capable of being transferred from the non-aligning position into the aligning position independently from each other.

In some embodiments according to the invention, the aligning device comprises or consists of a memory shape material.

In certain embodiments according to the invention, the aligning device of the apparatus comprises at least one open or closed loopy or wound section. The latter can have the form of a loop or sling.

The open or closed wound section may have the form of a pig tail, a spiral, a helix, or the like.

In some embodiments according to the invention, the apparatus comprises a reception area for receiving the implant.

In some embodiments according to the invention, the reception area is a shaft or has the form of a shaft.

The reception area can receive the implant releasably such that the implant can be delivered to the implantation site by means of the apparatus. After having reached the final implantation site, the implant may be released from the reception area optionally by using appropriate means or devices, respectively. Then, the implant stays at the implantation site while the reception area may be removed from the implantation site together with the other sections of the apparatus.

In certain embodiments according to the invention, the aligning device of the apparatus is connected or intended or provided and suited for a connection with a means or device, respectively, for releasing a fluid for medical imaging.

In some embodiments according to the invention, the implant is a stent and/or a cardiac valve arrangement.

In one embodiment according to the invention, the aligning device is designed or embodied as a spring, in particular as a spiral or coil spring, and/or is formed from an appropriate—preferably an elastic or flexible—material such as, e.g., a plastic material or gum.

In one embodiment of the apparatus according to the invention, the apparatus comprises at least two or at least three different passages or apertures, respectively.

When according to the invention at least two or three different passages or apertures, respectively, are mentioned, this can, in one embodiment according to the invention, refer to a respective different geometrical shape of the passages or apertures, respectively. In other words, the passages or apertures, respectively, may differ in their design.

In one embodiment according to the invention, the "three different passages or apertures, respectively" may differ in their area size.

In one embodiment according to the invention, a passage or aperture, respectively, is the open passage between an exterior of the apparatus or of the shaft of the apparatus and an interior of the apparatus or of the shaft of the apparatus.

In one embodiment according to the invention, the passages or apertures, respectively, may each comprise a range of geometrical designs. Thus, the passages or apertures, respectively, do not have to have an unchangeable design or size as long as the respective function (and optionally only this function) is possible within the respective range of the geometrical design. Within the limits predetermined by means of the range, the respective passages or apertures, respectively, may therefore—to all intents and purposes—be variable.

In one embodiment according to the invention, the apparatus is designed or embodied for folding and/or unfolding an implant that is, for example, a stent or a cardiac valve arrangement.

In one embodiment of the set according to the invention, the implant is a foldable and/or unfoldable implant.

In one embodiment of the method according to the invention, the method comprises transferring the aligning device from the non-aligning position into the aligning position and/or vice versa, after having inserted the apparatus at the implantation site.

In one embodiment of the method according to the invention, the method comprises directing a fluid for medical imaging through a lumen of the aligning device.

The advantages achievable by means of the apparatus according to the invention may also be obtained by means of the set according to the invention and the method according to the invention. Some or all of the following advantages may be achieved in some or in all of the embodiments according to the invention.

Among the advantages achievable according to the invention is that the mechanical stress or impairment of the tissue of the implantation site in general is in certain embodiments according to the invention at best only little.

This advantage can even be increased in that the aligning device or the aligning sections thereof are in some embodiments according to the invention wires or filaments, respectively, e.g., made from or comprising Nitinol, however, in any case, sections having a certain flexibility. This can also favor a gentle handling with the tissue of the implantation site as the mechanical stress applied on the tissue is low. Bleedings, wounds, irritations, and the like can be prevented.

One of the advantages achievable according to the invention is further that both implanting as well as imaging the implantation site is possible at the same time by using the apparatus in one embodiment according to the invention. In these embodiments, there is no further device or means required for this purpose in addition to the apparatus according to the invention for fulfilling both functions. This can both facilitate the handling of the required instruments as well as require an only smaller access or fewer accesses than the solutions known.

Another advantage is that, in some embodiments according to the invention, a proper alignment—or more proper as compared to the state of the art—to the morphology of the implantation site is possible. According to the invention, it is thus, e.g., possible to achieve an appropriate alignment even for two-part cardiac valves or the connection sites thereof with the heart muscle, respectively, as, due to the multiple separation of the aligning device, another number of aligning sections is used than is, e.g., provided or required for cardiac valves comprising three valves. Thus, in some embodiments according to the invention, if needed, e.g., not three but only two aligning sections may be used or transferred into the aligning position. Moreover, the two aligning sections used can exit the apparatus appropriately at positions being suitably spread across the periphery of the apparatus or the shaft thereof. This allows a further advantageous flexibility during use of the apparatus according to the invention in some of its embodiments. Thus, the latter can be used for, e.g., aligning any arbitrary one of the cardiac valve prostheses known during the implantation thereof.

A still further advantage of the present invention which can be achieved in certain embodiments is the simple match of the aligning device or the aligning sections thereof. This can, for example, be achieved by means of a memory shape (or shape memory, respectively) material. Thus, the aligning device or sections hereof may consist of Nitinol wires or filaments, respectively, that can be brought into an appropriate form easily, which they are able to reassume after omitting external limitations.

In the following, the present invention will be exemplarily described with reference to the accompanying drawing. In the drawing, identical reference numerals denote same or identical elements or components, respectively. In the drawing:

FIG. 1 shows a set 1 according to the invention comprising an apparatus 3 according to the invention of a first embodiment.

The apparatus 3 having an end portion and a tip 31 comprises a medical implant 6 and an aligning device 9.

Figure 1:
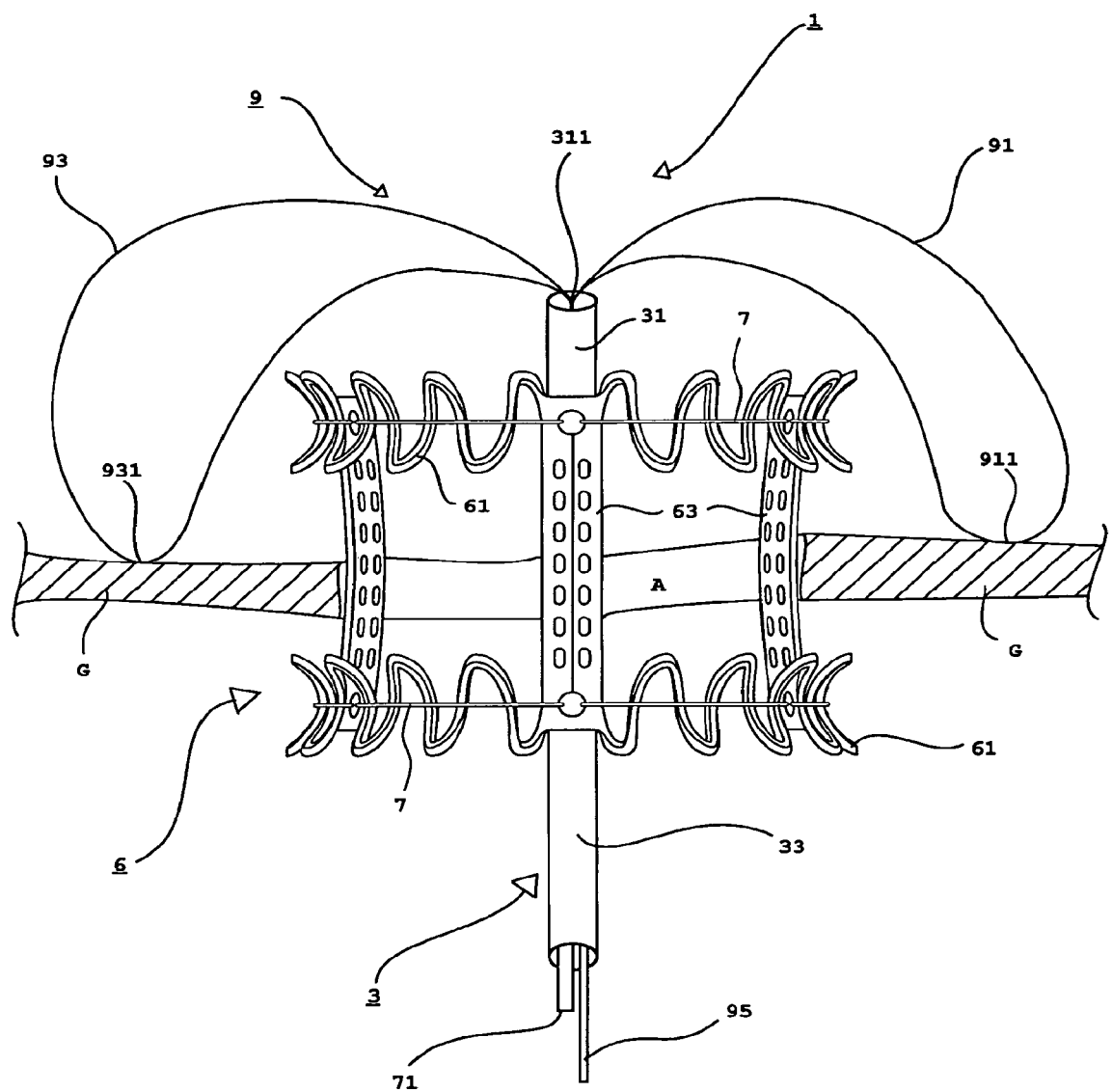
FIG. 1 shows a set according to the invention comprising an apparatus according to the invention in a first embodiment comprising a medical implant and an aligning device.

The implant 6 comprises two ring structures 61 that can be expanded or folded by means of threads 7. The threads 7 are guided through an interior of the apparatus 3 and can be actuated at a further end portion of the apparatus 3 as a continuation 71. The ring structures 61 are distanced from each other by means of struts 63 that are arranged between the ring structures 61. As can be recognized by a person skilled in the art, the implant 6 shown in FIG. 1 is just an arbitrary example of an implant selected for illustrative purposes. For details of the implant shown in FIG. 1 it is referred to WO 2009/109348 A1.

In the example of FIG. 1, the aligning device 9 comprises two aligning sections 91 and 93; however, according to the invention, more or fewer than two aligning sections could also be provided or intended.

The aligning sections 91, 93 of the representation of FIG. 1 are designed or embodied as wires or filaments, respectively, and in form of loops or slings, respectively, i.e., in form of closed structures. However, according to the invention, a closed structure is not required.

Each of the aligning sections 91, 93 is supported by the tissue G at a section 911 or 931 and thereby contacts tissue G. As the aligning sections 91, 93 show a stiffness resulting from their material and/or shape, they show a resistance during pulling back or retrieving, respectively, the apparatus 3 guided from the bottom through the tissue aperture A in FIG. 1. They hereby align the apparatus 3 relative to the tissue G or the tissue aperture A thereof by requiring an increased force for retrieving the apparatus 3 out of the tissue aperture A (i.e., in a downward direction in FIG. 1) or by even preventing such a retrieval.

After aligning the apparatus 3 as described above and thus the accompanying alignment of the implant 6 relative to the tissue G or the tissue aperture A, the implant 6 can be expanded by means of the threads 7 or the continuations 71 thereof, respectively. Subsequently—as well as at any other point of time—the aligning sections 91 and 93 may be pulled into an interior of the apparatus 3 by pulling a continuation 95 of the aligning sections 91 and 93. The loops or slings, respectively, of the aligning device 9, i.e., the aligning sections 91 and 93, shown in FIG. 1 are thus not present outside the apparatus 3 anymore. Therewith, the alignment is cancelled or offset. The apparatus 3 can be pulled downwards out of the tissue aperture A (after having released the implant 6 from the apparatus 3).

Figure 2:
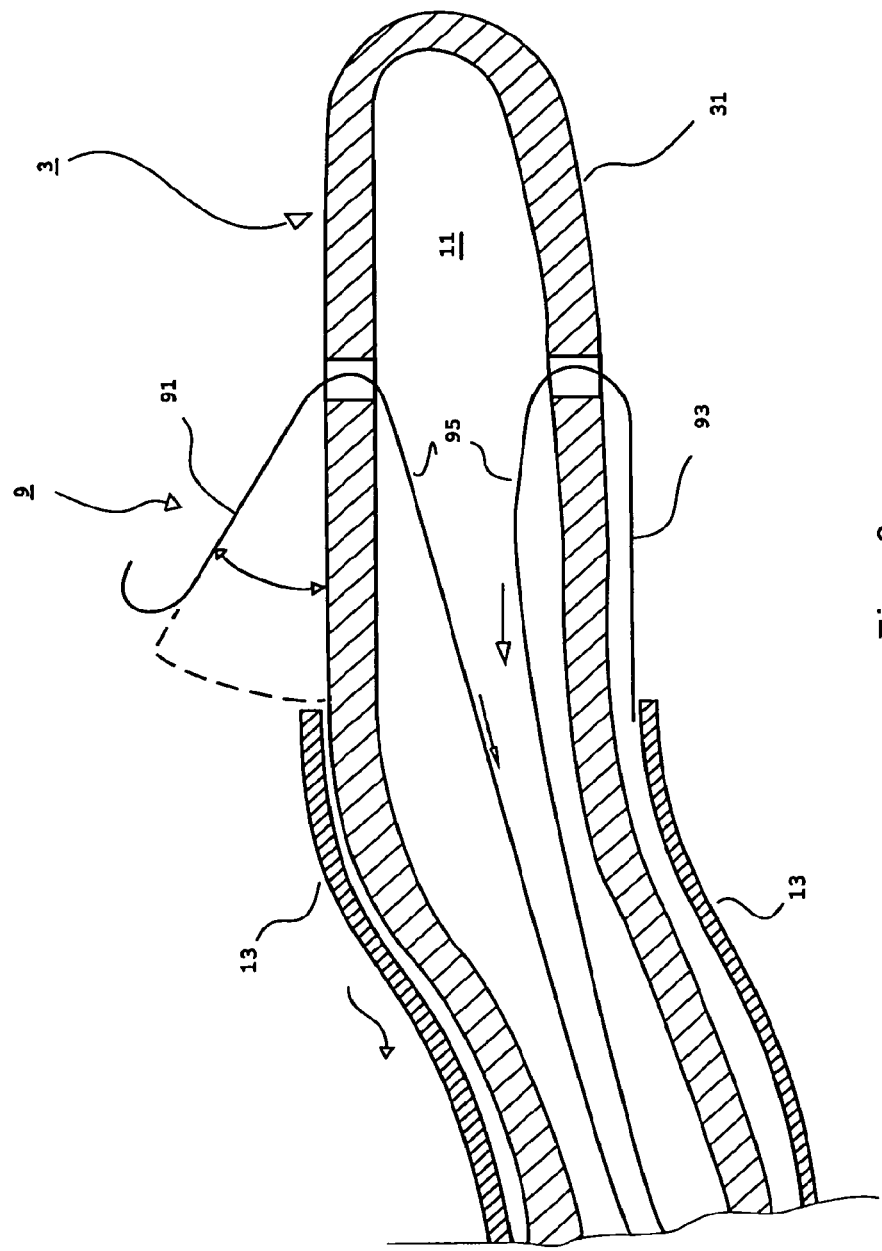
FIG. 2 shows an apparatus according to the invention in a second embodiment comprising a medical implant and an aligning device.

FIG. 2 shows an apparatus 3 according to the invention of a second embodiment comprising an end portion 31 and an interior 11. The apparatus 3 comprises an aligning device 9 comprising two aligning sections 91 and 93. The aligning sections 91 and 93 are continued within the interior 11 of the apparatus 3 in form of continuations 95 and can be pulled into, e.g., the interior 11 by means of the latter.

As compared to the apparatus 3 of FIG. 1, the apparatus 3 shown in FIG. 2 comprises a flexible or stiff sheath 13. The latter is movable relative to the shaft of the apparatus 3 by, e.g., being retrieved in the direction of the arrow (to the left border of FIG. 2).

When the sheath 13 is in a non-retrieved state, the aligning sections 91 and 93 are kept from lifting off the apparatus 3 or an outer surface thereof, respectively, which they would do otherwise due to their shape memory characteristics. By retrieving the sheath 13 in the direction of the arrow, the limitation on the moving or unfolding capability of the aligning sections 91 and 93 relative to the apparatus 3 is offset.

In FIG. 2 a state is shown in which the aligning section 91 could already be released from the apparatus 3 and transferred into its memory shape state after the sheath 13 having been retrieved. In the shape memory state predetermined by the manufacturing process, one end of the aligning section 91 lifts off the apparatus 3 and winds up in a C shape manner. According to the invention, any other shape into which the aligning section could wind up instead of a C shape is contemplated as well.

In the state shown in FIG. 2, the sheath 13 is not retrieved to a sufficient extent for also releasing the other aligning section 93. The latter still unchangedly contacts the apparatus 3 or an outer surface thereof, respectively. Only after the sheath has been pulled back a little bit further—not shown in FIG. 2—also the aligning section 93 will deform in an intended manner and be released from the outer surface of the apparatus 3.

Figure 3:
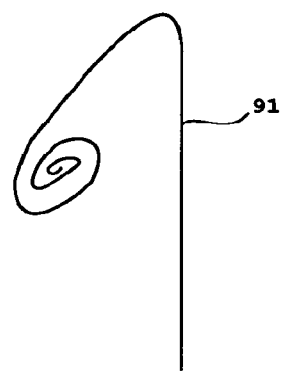
FIG. 3 shows an aligning section of an apparatus according to the invention in a further embodiment.

FIG. 3 shows an aligning section 91 of an apparatus according to the invention in a further embodiment. The aligning section 91 has a still further shape. The said may be referred to as spirally.

Figure 4:
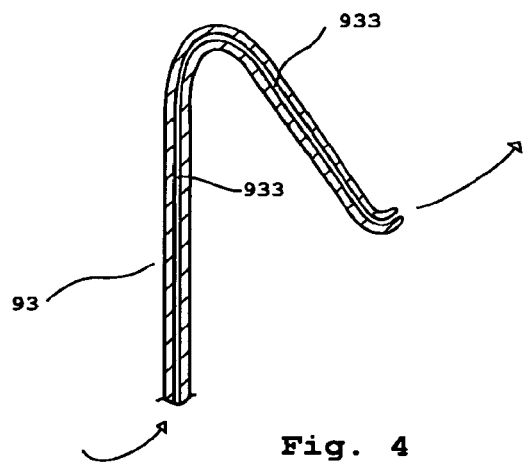
FIG. 4 shows an aligning section of an apparatus according to the invention in a still further embodiment.

FIG. 4 shows an aligning section 93 of an apparatus according to the invention in a still further embodiment.

The aligning section 93 has a still further geometrical outer shape.

The aligning section 93 further comprises a continuous lumen 933 within its interior. The latter extends along the whole length of the aligning section 93. According to the invention, in other embodiments, the lumen can, however, also only extend across a (part) portion of the aligning section 93.

In some embodiments, the lumen 933 is provided or intended to administer a fluid therethrough. The fluid can be a drug, a contrast agent, e.g., for imaging methods, or the like. The fluid can be introduced in and discharged out of the lumen along the directions of the arrows of FIG. 4. By means of the lumen, it is advantageously possible to use the aligning device both for aligning and for administering at the same time. In this way, introducing or inserting, respectively, an additional instrument for aligning or administering may advantageously be omitted.

As the aligning device is inserted together with the apparatus which is also used for inserting the implant into the body, inserting one or more further instruments for an alignment or an administration of an agent in addition to the apparatus may advantageously be omitted.

| Reference numeral list | |
|---|---|
| reference numeral | description |
| 1 | set |
| 11 | interior |
| 13 | sheath |
| 3 | apparatus |
| 31 | tip |
| 6 | medical implant |
| 61 | ring structures |
| 63 | struts |

-continued

Reference numeral list

| reference numeral | description |
| --- | --- |
| 7 | threads |
| 71 | continuation of the threads |
| 9 | aligning device |
| 91, 93 | aligning sections |
| 911, 931 | sections |
| 933 | lumen |
| 95 | continuation of the aligning sections |
| A | tissue aperture |
| G | tissue |

The invention claimed is:

1. A method for positioning an apparatus for implanting at least one medical implant at an implantation site located at cardiac valves within a patient's body, the implantation site having a tissue defined by a top surface and a bottom surface opposite to each other and an aperture extending through the top surface and the bottom surface, wherein the apparatus comprises a hollow shaft having a distal end, a sheath surrounding the shaft and an aligning device attached to the shaft, the aligning device comprising a plurality of aligning sections received within an interspace between the sheath and the shaft, each of the aligning sections having a first end located adjacent to the distal end and a second end spaced apart from the distal end, wherein the method comprises:
attaching the implant to the shaft, with the aligning sections being positioned closer to the distal end of the shaft than the implant;
advancing the apparatus with the implant attached thereto in a first direction to the implantation site, such that the distal end of the shaft and the aligning sections successively pass through the aperture of the tissue;
withdrawing the sheath in a second direction opposite to the first direction to expose the aligning sections, such that each of the aligning sections is released from the interspace and lifted from an outer radial surface of the shaft in such a way that the second end of the aligning section pivots about the first end and winds in a manner selected from one of a spiral shape and a C-shape;
aligning the apparatus relative to the aperture of the tissue by applying a force for retrieving the apparatus in the second direction, such that each of the aligning sections is engaged with the top surface of the tissue and the shaft is substantially perpendicular to a plane defined by the top surface, and the implant is positioned in the aperture of the tissue;
expanding the implant radially in the aperture of the tissue; and
retrieving the aligning device by pulling the plurality of aligning sections into an interior of the shaft after expansion of the implant.

2. The method according to claim 1, wherein the plurality of aligning sections comprises a first aligning section and a second aligning section, and wherein the step of withdrawing the sheath in the second direction further comprises:
pulling the sheath longitudinally with respect to the shaft in the second direction to a first position, such that the first aligning section is released from the interspace and lifted from the outer radial surface of the shaft, and the second aligning section remains received within the interspace; and then
further pulling the sheath in the second direction to a second position, such that the second aligning section is released from the interspace and lifted from the outer radial surface of the shaft.

3. The method according to claim 1, wherein after the plurality of aligning sections are released and engaged with the top surface of the tissue, the plurality of aligning sections show a resistance against the top surface of the tissue when a force is applied for retrieving the apparatus in the second direction.

4. The method according to claim 1, further comprising pulling the apparatus out of the aperture after retrieval of the aligning device.

5. The method according to claim 1, further comprising directing a fluid for medical imaging through a lumen of the aligning device.

6. The method according to claim 1, wherein the shaft further comprises a plurality of shaft apertures disposed at a side wall of the shaft, each of the aligning sections having the first end attached to one of the shaft apertures, the method further comprising retrieving the aligning device by pulling the plurality of aligning sections into an interior of the shaft through the shaft apertures after expansion of the implant.

7. The method according to claim 1, wherein each of the plurality of aligning sections is supported by the top surface of the tissue when the apparatus is aligned relative to the aperture of the tissue.

8. A method for positioning an apparatus for implanting at least one medical implant at an implantation site located at cardiac valves within a patient's body, wherein the apparatus comprises a hollow shaft having a distal end, a sheath surrounding the shaft and an aligning device attached to the shaft, the aligning device comprising a plurality of aligning sections received within an interspace between the sheath and the shaft, wherein the method comprises:
attaching the implant to the shaft, with the aligning sections being positioned closer to the distal end of the shaft than the implant;
advancing the apparatus with the implant attached thereto in a first direction to the implantation site, such that the distal end of the shaft and the aligning sections successively pass through the aperture of the tissue;
pulling the sheath longitudinally with respect to the shaft in a second direction to a first position, the second direction being opposite to the first direction, such that the first aligning section is released from the interspace and lifted from the outer radial surface of the shaft, and the second aligning section remains received within the interspace;
further pulling the sheath in the second direction to a second position, such that the second aligning section is released from the interspace and lifted from the outer radial surface of the shaft;
aligning the apparatus relative to the aperture of the tissue by applying a force for retrieving the apparatus in the second direction, such that each of the aligning sections are engaged with the tissue and the shaft is substantially perpendicular to the tissue, and the implant is positioned in the aperture of the tissue;
expanding the implant radially in the aperture of the tissue; and
retrieving the aligning device by pulling the plurality of aligning sections into an interior of the shaft after expansion of the implant.

9. The method according to claim 8, wherein each of the aligning sections has a first end located adjacent to the distal end and a second end spaced apart from the distal end, wherein after the aligning section is released from the interspace, the second end of the aligning section pivots about the first end and winds in a manner selected from one of a spiral shape and a C-shape.

10. The method according to claim 8, wherein after the plurality of aligning sections are released and engaged with the tissue, the plurality of aligning sections show a resistance against the tissue when a force is applied for retrieving the apparatus in the second direction.

11. The method according to claim 8, further comprising pulling the apparatus out of the aperture after retrieval of the aligning device.

12. The method according to claim 8, further comprising directing a fluid for medical imaging through a lumen of the aligning device.

13. The method according to claim 8, wherein the shaft further comprises a plurality of shaft apertures disposed at a side wall of the shaft, each of the aligning sections being attached to one of the shaft apertures, the method further comprising retrieving the aligning device by pulling the plurality of aligning sections into an interior of the shaft through the shaft apertures after expansion of the implant.

14. The method according to claim 8, wherein each of the plurality of aligning sections is supported by the tissue when the apparatus is aligned relative to the aperture of the tissue.

15. A method for positioning an apparatus for implanting at least one medical implant at an implantation site located at cardiac valves within a patient's body, the implantation site having a tissue defined by a top surface and a bottom surface opposite to each other and an aperture extending through the top surface and the bottom surface, wherein the apparatus comprises a hollow shaft having a distal end, a sheath surrounding the shaft and an aligning device attached to the shaft, the aligning device comprising a plurality of aligning sections received within an interspace between the sheath and the shaft, each of the aligning sections having a first end located adjacent to the distal end and a second end spaced apart from the distal end, wherein the method comprises:
    attaching the implant to the shaft, with the aligning sections being positioned closer to the distal end of the shaft than the implant;
    advancing the apparatus with the implant attached thereto in a first direction to the implantation site, such that the distal end of the shaft and the aligning sections successively pass through the aperture of the tissue;
    withdrawing the sheath in a second direction opposite to the first direction to expose the aligning sections, such that each of the aligning sections is released from the interspace and lifted from an outer radial surface of the shaft in such a way that the second end of the aligning section pivots about the first end and winds in a manner selected from one of a spiral shape and a C-shape;
    aligning the apparatus relative to the aperture of the tissue by applying a force for retrieving the apparatus in the second direction, such that each of the aligning sections is engaged with the top surface of the tissue and the shaft is substantially perpendicular to a plane defined by the top surface, and the implant is positioned in the aperture of the tissue;
    expanding the implant radially in the aperture of the tissue; and
    directing a fluid for medical imaging through a lumen of the aligning device.

16. The method according to claim 15, wherein the plurality of aligning sections comprises a first aligning section and a second aligning section, and wherein the step of withdrawing the sheath in the second direction further comprises:
    pulling the sheath longitudinally with respect to the shaft in the second direction to a first position, such that the first aligning section is released from the interspace and lifted from the outer radial surface of the shaft, and the second aligning section remains received within the interspace; and then
    further pulling the sheath in the second direction to a second position, such that the second aligning section is released from the interspace and lifted from the outer radial surface of the shaft.

17. The method according to claim 15, wherein after the plurality of aligning sections are released and engaged with the top surface of the tissue, the plurality of aligning sections show a resistance against the top surface of the tissue when a force is applied for retrieving the apparatus in the second direction.

18. The method according to claim 15, further comprising:
    retrieving the aligning device by pulling the plurality of aligning sections into an interior of the shaft after expansion of the implant; and
    pulling the apparatus out of the aperture after retrieval of the aligning device.

19. The method according to claim 15, wherein the shaft further comprises a plurality of shaft apertures disposed at a side wall of the shaft, each of the aligning sections having the first end attached to one of the shaft apertures, the method further comprising retrieving the aligning device by pulling the plurality of aligning sections into an interior of the shaft through the shaft apertures after expansion of the implant.

20. The method according to claim 15, wherein each of the plurality of aligning sections is supported by the top surface of the tissue when the apparatus is aligned relative to the aperture of the tissue.

* * * * *